(12) United States Patent
Lorenz et al.

(10) Patent No.: US 7,655,692 B2
(45) Date of Patent: Feb. 2, 2010

(54) PROCESS FOR FORMING AMORPHOUS ATORVASTATIN

(75) Inventors: Douglas A. Lorenz, Bend, OR (US); Kenneth Craig Waterman, Easy Lyme, CT (US)

(73) Assignee: Pfizer Inc., New York, NY (US)

( * ) Notice: Subject to any disclaimer, the term of this patent is extended or adjusted under 35 U.S.C. 154(b) by 795 days.

(21) Appl. No.: 10/828,488

(22) Filed: Apr. 20, 2004

(65) Prior Publication Data

US 2005/0032880 A1 Feb. 10, 2005

Related U.S. Application Data

(60) Provisional application No. 60/477,916, filed on Jun. 12, 2003.

(51) Int. Cl.
*A61K 31/401* (2006.01)
*C07D 207/34* (2006.01)

(52) U.S. Cl. ........................ 514/423; 548/537

(58) Field of Classification Search ................ 548/563, 548/537; 514/427, 423
See application file for complete search history.

(56) References Cited

U.S. PATENT DOCUMENTS

| | | |
|---|---|---|
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,686,104 A | 11/1997 | Mills et al. |
| 5,969,156 A | 10/1999 | Briggs et al. |
| 5,998,633 A | 12/1999 | Jacks et al. |
| 6,087,511 A | 7/2000 | Lin et al. |
| 6,121,461 A | 9/2000 | McKenzie |
| 6,126,971 A | 10/2000 | Mills et al. |
| 6,248,363 B1 | 6/2001 | Patel et al. |
| 6,274,740 B1 | 8/2001 | Lin et al. |
| 6,395,300 B1 | 5/2002 | Straub et al. |
| 6,433,213 B1 | 8/2002 | Bosch et al. |
| 6,476,235 B2 | 11/2002 | Butler et al. |
| 6,531,507 B1 | 3/2003 | Pflaum et al. |
| 6,605,729 B1 | 8/2003 | Byrn et al. |
| 2003/0109584 A1 | 6/2003 | Pflaum et al. |

FOREIGN PATENT DOCUMENTS

| | | |
|---|---|---|
| EP | 0 848 705 B1 | 2/1997 |
| EP | 1 027 886 A2 | 8/2000 |
| WO | WO 97/03960 | 2/1997 |
| WO | WO 00/71116 A1 | 11/2000 |
| WO | WO 00/72825 A1 | 12/2000 |
| WO | WO 01/28999 A1 | 4/2001 |
| WO | WO 01/36384 A1 | 5/2001 |
| WO | WO-01/42209 A1 * | 6/2001 |
| WO | WO 01/42209 A1 | 6/2001 |
| WO | WO 02/41834 A2 | 5/2002 |
| WO | WO 02/43667 A2 | 6/2002 |
| WO | WO 02/43732 A1 | 6/2002 |
| WO | WO 02/051385 A1 | 7/2002 |
| WO | WO 02/051804 A1 | 7/2002 |
| WO | WO 02/057228 A1 | 7/2002 |
| WO | WO 02/057229 A1 | 7/2002 |
| WO | WO 02/057274 A1 | 7/2002 |
| WO | WO 02/059087 A1 | 8/2002 |
| WO | WO 02/062824 A2 | 8/2002 |
| WO | WO 02/083637 A1 | 10/2002 |
| WO | WO 02/083638 A1 | 10/2002 |
| WO | WO 03/011826 A1 | 2/2003 |
| WO | WO 03/018547 A2 | 3/2003 |
| WO | WO 03/050085 A1 | 6/2003 |
| WO | WO 03/070702 A1 | 8/2003 |
| WO | WO 2004/022053 A1 | 3/2004 |

OTHER PUBLICATIONS

Gaspar et al, "Spray drying technology for better API crystals," Process Development, 2004.*
Takemoto, M., et al, "Statinsas antioxidant therapy for preventing cardiac myocyte hypertrophy", The Journal of Clinical Investigation, Nov. 2001, vol. 108, No. 10, pp. 1429-1437.
Konno, T., Chem. Pharm. Bull., 1990, vol. 38, pp. 2003-2007.

* cited by examiner

*Primary Examiner*—Rebecca L Anderson
*Assistant Examiner*—Joseph R Kosack
(74) *Attorney, Agent, or Firm*—Gregg C. Benson; B. Timothy Creagan

(57) ABSTRACT

Forming amorphous atorvastatin comprises the steps of dissolving atorvastatin in a hydroxylic solvent, followed by rapidly evaporating the solvent. In another aspect, a composition comprises particles of amorphous atorvastatin and a core.

14 Claims, 3 Drawing Sheets

PROCESS FOR FORMING AMORPHOUS ATORVASTATIN

CROSS-REFERENCE TO RELATED APPLICATIONS

This application claims priority from U.S. Provisional Patent Application No. 60/477,916 filed Jun. 12, 2003.

FIELD OF THE INVENTION

The invention relates to processes for forming amorphous atorvastatin using hydroxylic solvents, and to compositions comprising amorphous atorvastatin.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium is currently sold as Lipitor® having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

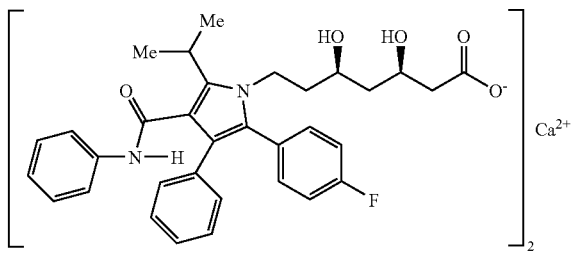

Atorvastatin and pharmaceutically acceptable salts thereof are selective, competitive inhibitors of HMG-CoA reductase. As such, atorvastatin calcium is a potent lipid lowering compound and is thus useful as a hypolipidemic and/or hypocholesterolemic agent, as well as in the treatment of osteoporosis, benign prostatic hyperplasia (BPH), and Alzheimer's disease.

A number of patents have issued disclosing atorvastatin, formulations of atorvastatin, as well as processes and key intermediates for preparing atorvastatin. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Additionally, a number of published International Patent Applications and patents have disclosed crystalline forms of atorvastatin, as well as processes for preparing amorphous atorvastatin. These include: U.S. Pat. No. 5,969,156; U.S. Pat. Nos. 6,121,461; 6,605,759; WO 01/36384; WO 02/41834; WO 02/43667; WO 02/43732; WO 02/051804; WO 02/057228; WO 02/057229; WO 02/057274; WO 059087; WO 02/083637; WO 02/083638; WO 03/011826; WO 03/050085; WO 03/07072; and WO 04/022053.

It has been disclosed that the amorphous forms of a number of drugs exhibit different dissolution characteristics and in some cases different bioavailability patterns compared to the crystalline form (Konno T., Chem. Pharm. Bull., 1990;38: 2003-2007). For some therapeutic indications one bioavailability pattern may be favored over another.

Variations in dissolution rates can make it advantageous to produce atorvastatin formulations in either crystalline or amorphous forms. For example, for some potential uses of atorvastatin (e.g., acute treatment of patients having strokes as described in Takemoto, M.; Node, K.; Nakagami, H.; Liao, Y.; Grimm, M.; Takemoto, Y.; Kitakaze, M.; Liao, J. K., Journal of Clinical Investigation, 2001; 108(10): 1429-1437) a rapid onset of activity may be highly beneficial in improving the efficacy of the atorvastatin.

The preparation of amorphous atorvastatin has been previously disclosed. For example, Lin et al., U.S. Pat. No. 6,087,511 disclose forming amorphous atorvastatin from crystalline atorvastatin. To form amorphous atorvastatin, Lin et al. disclose that crystalline atorvastatin is dissolved in a non-hydroxylic solvent such as tetrahydrofuran. The non-hydroxylic solvent is removed to produce a brittle foam that is broken up by mechanical agitation to afford amorphous atorvastatin.

WO 00/71116 also discloses forming amorphous atorvastatin using a non-hydroxylic solvent.

WO 01/28999 discloses a process for forming amorphous atorvastatin by recrystallization of crude atorvastatin from an organic solvent which comprises dissolving crude amorphous atorvastatin calcium in a lower alkanol containing 2-4 carbon atoms or a mixture of such alkanols under heating. The amorphous atorvastatin calcium is precipitated after cooling.

WO 01/42209 discloses preparing amorphous atorvastatin by precipitating the atorvastatin using a solvent in which atorvastatin is insoluble or very slightly soluble, from a solution of atorvastatin which is provided with a solvent in which atorvastatin is freely soluble. Preferred solvents in which atorvastatin is freely soluble include low molecular weight alcohols, e.g. methanol and ethanol.

U.S. Pat. No. 6,531,507 B1 and U.S. 2003/0109584 A1 disclose HMG-CoA reductase inhibitors that are stabilized by forming a homogeneous composition with a buffering substance or basifying substance. The HMG-CoA reductase inhibitor and buffering substance or basifying substance are crystallized or co-precipitated from the same medium.

The current processes for production of amorphous atorvastatin involve solvents which are not optimal due to toxicity or environmental concerns. In addition, current processes are not optimal in terms of production capabilities. Therefore, there remains a continuing need for improved methods for preparation of amorphous atorvastatin.

SUMMARY OF THE INVENTION

A process for forming amorphous atorvastatin comprises the steps of: (a) dissolving atorvastatin in a solution comprising a hydroxylic solvent and (b) rapidly evaporating the hydroxylic solvent from the solution to form amorphous atorvastatin.

In a preferred embodiment, the resulting amorphous atorvastatin is in the form of small particles ranging in size from 1 μm to 1000 μm.

In a preferred method, the solvent is removed by spray drying.

We have found that, unexpectedly, hydroxylic solvents can indeed be employed in evaporative formation of amorphous atorvastatin. More specifically, amorphous material is formed when the atorvastatin is dissolved in a solution containing a hydroxylic solvent, and the hydroxylic solvent is rapidly evaporated. The use of a hydroxylic solvent provides one or more of the following advantages. Atorvastatin has good solubility in hydroxylic solvents, thus potentially improving the efficiency of the process for forming amorphous material by reducing the amount of solvent needed. The use of hydroxylic solvents has the additional advantage that such solvents are easy to evaporate to low residual solvent levels. Such solvents also tend to be less toxic than non-hydroxylic solvents, and thus acceptable residual solvent levels may be higher than would be the case for material formed using non-hydroxylic solvents. In addition, the small particle size achieved by these rapid formation processes alleviates the need for a milling step, thereby reducing the number of unit operations in production of the material for commercial use.

Rapid evaporation achieves yet another advantage, which is the formation of particles having relatively uniform particle size distribution and shape. Amorphous atorvastatin formed by mechanically breaking apart a glassy foam tends to have a wide size distribution, and the individual particles tend to have rough or sharp edges. In contrast, particles formed by rapid evaporation tend to be rounder and have narrower size distributions. The particles formed by rapid evaporation have better flow characteristics and are less likely to become segregated during manufacturing, such as during handling to form tablets or other dosage forms. This is particularly important for a drug like atorvastatin, since the drug itself has a high potency and therefore is often used at a low dose. Reducing segregation during manufacture of the dosage form is important to ensure uniformity of dose in the dosage form. Thus, the present invention may reduce segregation during manufacturing of the dosage form by providing amorphous atorvastatin that is easier to handle. The use of amorphous atorvastatin produced by rapid evaporation in unit dosage forms is disclosed in copending, commonly assigned patent applications entitled "Pharmaceutical Compositions of Atorvastatin," (Ser. No. 10/828,419, Ser. No. 10/828,079, and Ser. No. 10/828,398) filed concurrently herewith.

The small particle size achieved by rapid evaporation is also believed to yield particles that have more rapid dissolution characteristics. This may be due to the high surface area of the small particles.

In a separate aspect of the invention, a composition comprises amorphous atorvastatin layered on solid core.

The foregoing and other objectives, features and advantages of the invention will be more readily understood upon consideration of the following detailed description of the invention.

DETAILED DESCRIPTION OF THE INVENTION

Figure 1:
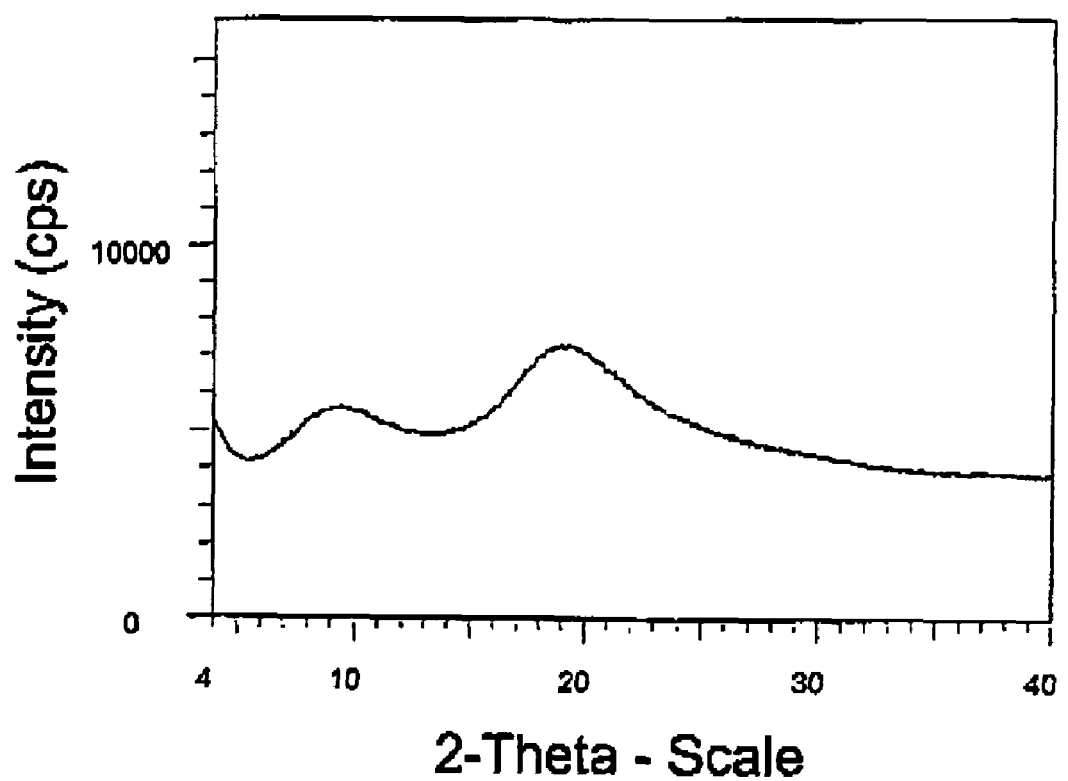
FIG. 1 shows a powder X-ray diffraction (PXRD) diffractogram of amorphous atorvastatin made in Example 1.

The present process involves dissolving atorvastatin in a solution, such as a spray solution, followed by rapid evaporation to form amorphous atorvastatin. As will be recognized by those skilled in the art, the initial atorvastatin which is dissolved to form the spray solution may be in any morphological form such as, for example, crystalline or amorphous, as well as disordered crystals, liquid crystals, plastic crystals, mesophases, and the like, or any combination thereof. Atorvastatin may readily be prepared, for example, as described in U.S. Pat. Nos. 4,681,893, 5,273,995 and 5,969,156 which are incorporated herein by reference. The term "atorvastatin" includes the free acid form, salt forms, solvates, hydrates and polymorphs. Pharmaceutically acceptable base addition salts of atorvastatin are formed with metals or amines, such as alkali and alkaline earth metals or organic amines. Examples of metals used as cations are sodium, potassium, magnesium, calcium, and the like. Examples of suitable amines are N,N1-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts", J. of Pharm. Sci., 1977; 66:1).

A preferred form of atorvastatin is atorvastatin hemi-calcium salt trihydrate, sold under the tradename LIPITOR®.

Amorphous atorvastatin is formed by solvent processing using a hydroxylic solvent. Hydroxylic solvents are organic solvents containing a hydroxy group. Solvents suitable for solvent processing can be any hydroxylic solvent in which the atorvastatin is soluble. Preferably, atorvastatin has a solubility of at least 1 weight percent (wt %), and more preferably at least 5 wt % in the hydroxylic solvent. Preferably, the solvent is also volatile with a boiling point of 150° C. or less. In addition, the solvent should have relatively low toxicity and be removed from the amorphous atorvastatin to a level that is acceptable according to The International Committee on Harmonization (ICH) guidelines. Removal of solvent to this level may require a subsequent processing step such as tray-drying. Preferred hydroxylic solvents include methanol, ethanol, n-propanol, and iso-propanol. The solvent may be a mixture of hydroxylic solvents.

Amorphous atorvastatin is formed by dissolving atorvastatin in a solution comprising the hydroxylic solvent, and then rapidly evaporating the solvent. As discussed above, atorvastatin may be in any crystalline or non-crystalline form prior to being dissolved in solution. The solution may contain from 0.1 to 30 wt % atorvastatin, or up to the solubility of atorvastatin in the solvent if the solubility is lower. We have found that 5 wt % atorvastatin works well. The solvent may also contain low levels of additives. Additives are preferably present at less than 30% of the atorvastatin (w:w); more preferably less than 15% of the atorvastatin (w:w). Examples of such additives include antioxidants, surfactants, dispersants, lubricants, and other stabilizing additives.

Exemplary processes for rapidly evaporating solvent are spray-drying, spray-coating (pan-coating, fluidized bed coating, etc.), drum drying and wiped film drying. In addition to the hydroxylic solvent, the solution may contain other liquids so long as the atorvastatin remains sufficiently soluble in the solution. For example, the solution may contain up to 30 wt % water. In addition, the solution may contain a non-hydroxylic solvent up to 50 wt %. Preferably, the atorvastatin is dissolved in a solution comprising at least 50 wt % hydroxylic solvent, more preferably at least 60 wt % hydroxylic solvent, and even more preferably at least 70 wt % hydroxylic solvent.

A key feature of the present invention is that the solvent is rapidly removed from the solution to form amorphous atorvastatin. By rapid removal of the solvent is meant that the solvent is removed from the solution sufficiently fast so that at least 90 wt % of the solvent is removed within 5 minutes, preferably within one minute, and more preferably within 20 seconds. Rapid removal of the solvent achieves amorphous drug which is less likely to contain crystalline drug. The amount of crystalline material present in the resulting amorphous drug is small. Preferably at least 90 wt %, more preferably at least 95 wt %, and even more preferably at least 99 wt % of the resulting drug is amorphous after rapid evaporation of the solvent. Amorphous material, and the amount of amorphous material present, may be characterized by techniques known in the art such as powder x-ray diffraction (PXRD), solid state nuclear magnetic resonance (SSNMR) spectroscopy, or thermal techniques such as differential scanning calorimetry (DSC).

A spray-drying process may be used to form amorphous atorvastatin. The atorvastatin is dissolved in a hydroxylic solvent and then sprayed in a spray-drying apparatus where the solvent is rapidly evaporated, forming solid particles of amorphous atorvastatin. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in *Perry's Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atmospheres (atm); or (2) mixing the liquid droplets with a warm drying gas; or (3) both (1) and (2). In addition, at least a portion of the heat required for evaporation of solvent may be provided by heating the spray solution.

The atorvastatin solution feed can be spray-dried under a wide variety of conditions and yet still yield amorphous atorvastatin. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) and do not stick to or coat the spray-drying chamber wall.

Although the maximum droplet size varies widely as a function of the size, shape and flow pattern within the spray-dryer, generally droplets should be less than about 500 μm in diameter when they exit the nozzle. Examples of types of nozzles that may be used to form the droplets include the two-fluid nozzle, the fountain-type nozzle, the flat fan-type nozzle, the pressure nozzle and the rotary atomizer. In one embodiment, a pressure nozzle is used. Use of pressure nozzles to form spray-dried amorphous materials are disclosed in detail in commonly assigned copending U.S. Provisional Application No. 60/353,986 (Attorney docket No. PC23203), the disclosure of which is incorporated herein by reference.

The solution can be delivered to the spray nozzle or nozzles at a wide range of temperatures and flow rates. Generally, the solution temperature can range anywhere from just above the solvent's freezing point to about 20° C. above its ambient pressure boiling point (by pressurizing the solution) and in some cases even higher. Solution flow rates to the spray nozzle can vary over a wide range depending on the type of nozzle, spray-dryer size and spray-dry conditions such as the inlet temperature and flow rate of the drying gas. Generally, the energy for evaporation of solvent from the solution in a spray-drying process comes primarily from the drying gas.

The drying gas can, in principle, be essentially any gas, but for safety reasons and to minimize undesirable oxidation of the atorvastatin, an inert gas such as nitrogen, nitrogen-enriched air or argon is preferably utilized. The drying gas is typically introduced into the drying chamber at a temperature between about 60° C. and about 300° C. and preferably between about 80° C. and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous amorphous material, in contrast to material comprising crystalline and amorphous atorvastatin. In a preferred embodiment, the height and volume of the spray-dryer are adjusted to provide sufficient time for the droplets to dry prior to impinging on an internal surface of the spray-dryer, as described in detail in commonly assigned, copending U.S. Provisional Application No. 60/354,080, the disclosure of which is incorporated herein by reference.

Following solidification, the resulting solid powder of amorphous atorvastatin typically stays in the spray-drying chamber for about 5 to 60 seconds, further evaporating solvent from the solid powder. The final residual solvent level of the amorphous atorvastatin as it exits the dryer should be low. Generally, the solvent level of the amorphous atorvastatin as it leaves the spray-drying chamber should be less than 10 wt % and preferably less than 2 wt %. Following formation, the amorphous atorvastatin can be dried to remove residual solvent using a suitable drying process, such as tray drying, fluid bed drying, microwave drying, belt drying, rotary drying, and other drying processes known in the art. The final residual solvent level is preferably less than 1 wt %, preferably less than 0.1 wt %.

The resulting spray dried amorphous atorvastatin is usually in the form of small particles. The mean size of the particles may be less than 1000 μm in diameter, or less than 500 μm in diameter, or less than 100 μm in diameter, or less than 50 μm in diameter or less than 25 μm in diameter.

Another useful parameter is "Span," defined as $$\text{Span} = \frac{D_{90} - D_{10}}{D_{50}},$$

where $D_{50}$ is the diameter corresponding to the diameter of particles that make up 50% of the total volume of particles of equal or smaller diameter, $D_{90}$ is the diameter corresponding to the diameter of particles that make up 90% of the total volume of particles of equal or smaller diameter, and $D_{10}$ is the diameter corresponding to the diameter of particles that make up 10% of the total volume of particles of equal or smaller diameter. Span, sometimes referred to in the art as the Relative Span Factor or RSF, is a dimensionless parameter indicative of the uniformity of the particles size distribution. Generally, the lower the Span, the more narrow the size distribution, resulting in improved flow characteristics. Preferably, the Span of the particles produced by the process is less than about 3, more preferably less than about 2.5, and most preferably less than about 2.0.

Once the amorphous atorvastatin has been formed several processing operations can be used to facilitate incorporation of the amorphous atorvastatin into a dosage form. These processing operations include drying, granulation, and milling. Preferred dosage forms include sachets, tablets, fast-dissolving dosage forms, chewable dosage forms, and capsules.

In a separate aspect of the invention, the amorphous atorvastatin may also be made by spray coating. The term "spray coating" is used conventionally and refers to the coating or layering of the amorphous atorvastatin onto a core. The term core is used broadly to describe any solid substrate onto which the atorvastatin solution may be sprayed, so that the amorphous atorvastatin forms as a layer on the core. In this process, the atorvastatin is dissolved in a hydroxylic solvent as described above. Preferably, the core has a solubility in the spray-coating solution of less than 10 wt %; more, preferably less than 5 wt %; still more preferably less than 1 wt %.

The core may be pharmaceutically inert. The core may be a solid particle or object, which does not disintegrate in the relevant body fluid. Alternatively, the core may comprise a disintegrating agent which will cause the layered particle to disrupt in the relevant body fluid. The core is mainly intended for carrying the layer(s) of amorphous atorvastatin. Examples of core materials are non-pareil seeds, sugar beads, wax beads, glass beads, lactose, microcrystalline cellulose, polymer beads, starch, colloidal silica, calcium phosphate, calcium carbonate, and calcium containing salts and excipients, etc. The core may be made by any known method, such as melt- or spray-congealing, extrusion/spheronization, granulation, spray-drying and the like. Alternatively, the core may be a dosage form such as a tablet, pill, multiparticulate or capsule. The dosage form may contain atorvastatin or a different drug, and may provide either immediate or controlled release. Spray-coating amorphous atorvastatin onto the dosage form may be useful for a combination therapy of atorvastatin and another drug.

The cores may have any shape, size, and size distribution. In one embodiment, the core is generally spherical with a smooth surface. In another embodiment, the cores range in size of from about 1 μm to about 3000 μm, preferably from about 10 μm to about 1000 μm, more preferably from about 50 μm to about 500 μm. To obtain a uniform final product it is generally desired to use cores with a narrow size distribution. The core may be an agglomerate, a granule, or a particle which has been layered with one or more layer(s) in accordance with the invention. Core agglomerates and granules can be made by any method conventionally used in the art, such as spray-drying, vacuum drying, or spray granulation.

Atorvastatin solution may be sprayed using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-sprayers available from Glatt Air Technologies of Ramsey, N.J. and from Niro Pharma Systems of Bubendorf, Switzerland) and rotary granulators (e.g., CF-Granulator, available from Freund Corp). The spray nozzle can be placed in the top, side walls or the bottom of the spraying chamber and the chamber can be provided with more than one nozzle.

The core particles may be suspended in the gas in any convenient manner. The core particle may be carried upwards from the bottom of the spraying chamber by a suitable stream of gas. The gas suspended core particles are then hit by one or more small droplets ejected from the nozzle. In one embodiment, the spray solution is directed in the same direction as the suspending gas.

After spraying, the solvent provided on the cores is evaporated to obtain a deposit or layer of amorphous atorvastatin on the core. It is preferred that the chamber the coating is effected in is also used for the evaporation of the liquid. In one embodiment, the cores may be moved through the spraying zone to an evaporation zone for drying the layered cores using the gas in which the cores are suspended.

The gas in which the cores are suspended may be the drying gas. During the movement upwards in the chamber and following spraying, the solvent is rapidly evaporated. Rapid evaporation is important to assure the atorvastatin is produced in an amorphous form. Preferably, the solvent is removed from the coated cores such that at least 90% of the solvent is removed within five minutes; more preferably within one minute. Rapid solvent removal also serves to prevent the particles from adhering to one another upon exiting the chamber.

Following sufficient evaporation of the solvent, the particles may be subject to a renewed treatment of spraying and evaporation, either immediately or after storage of the coated cores. The treatment of the coated cores continues until a predetermined particle size or weight is obtained. The determination of the desired particle size or weight can be conducted in accordance with known classification procedures. Alternately, a predetermined amount of the cores is sprayed with a predetermined amount of solution to produce the coated cores with the desired size or weight, or to achieve a desired concentration or potency of atorvastatin.

Spray coated cores of amorphous atorvastatin have the additional advantage of forming dense, large particles. As described above, atorvastatin is a high potency, low dose drug, and thus reducing segregation during manufacture of the drug is important to ensure good dose uniformity in the manufactured dosage forms. Coating amorphous atorvastatin onto cores may facilitate handling by providing large, dense particles which are less likely to become segregated during manufacture than pure amorphous material. In addition, such coated cores also have round surfaces and narrow size distributions, which improves flow characteristics and facilitates handling.

In addition, for coated cores where the cores comprise a dosage form, such as tablets, pills, multiparticulates, or capsule, further coatings can be applied. Such coatings can be used to impart a desired drug release property, or provide for improved handling, taste masking, flow, identification, or other such benefits.

The present invention relates to the treatment of diseases and conditions in a subject, such as, hyperlipidemia and/or hypercholesterolemia, osteoporosis, benign prostatic hyperplasia (BPH), and Alzheimer's disease with amorphous atorvastatin or a pharmaceutically acceptable salt thereof as described above that may be administered in a solid dosage form and/or contained in a therapeutic package or kit. The kit may include the solid dosage form and a container. Typically, the kit includes directions for administration of the dosage form. The container can be in any conventional shape or form as known in the art, for example, a paper box, a glass or plastic bottle, or a blister pack with individual dosage for pressing out of the back according to a therapeutic schedule.

Other features and embodiments of the invention will become apparent from the following examples which are given for illustration of the invention rather than for limiting its intended scope.

EXAMPLE 1

Amorphous atorvastatin was prepared by a spray-drying process using the following procedure. A 50 g sample of atorvastatin hemicalcium trihydrate (U.S. Pat. No. 5,273,995) was dissolved in 950 g of methanol to form feed solution comprising 5 wt % atorvastatin. The feed solution was pumped by a high-pressure gear pump (Bran Luebbe N—P31) to a Niro PSD-1 Spray-Dryer with a liquid feed process vessel and a pressure nozzle (Model SK 76-16 from Spraying Systems, Inc.). The dryer was also equipped with a 9-inch drying chamber extension to increase the length and volume of the dryer's drying chamber. The added length increased the particle residence time within the dryer. The dryer was also equipped with gas-dispersing means for introduction of the drying gas to the drying chamber. The gas-dispersing means consisted of a plate coextensive with the interior of the drying chamber (about 0.8 m diameter) and bearing a multiplicity of 1.7 mm perforations occupying about 1% of the surface area of the plate. The perforations were uniformly distributed across the plate, except that the density of perforations at the center 0.2 m of the diffuser plate was about 25% of the density of perforations in the outer part of the diffuser plate. The use of the diffuser plate resulted in organized plug flow of drying gas through the drying chamber and dramatically decreased product recirculation within the spray drier. The pressure nozzle was arranged flush with the gas disperser plate during operation. The spray solution was pumped to the spray drier at 160 g/min at a pressure of 12 atmosphere (atm) (160 pounds per square inch (psig)). Nitrogen drying gas was delivered to the gas disperser plate at an inlet temperature of 195° C. The evaporated solvent and drying gas exited the dryer at a temperature of 60±2° C. The amorphous atorvastatin formed by this process was collected in a cyclone and then dried in a solvent tray dryer by spreading the spray-dried particles onto polyethylene-lined trays to a depth of not more than 1 cm and then drying them at 40° C. for 16 hours.

A sample of the so-formed amorphous atorvastatin was examined using powder x-ray diffraction (PRXD) using a Bruker AXS D8 Advance diffractometer. Samples (approximately 100 mg) were packed in Lucite sample cups fitted with Si(511) plates as the bottom of the cup to give no background signal. Samples were spun in the $\phi$ plane at a rate of 30 revolutions per minute (rpm) to minimize orientation effects. The x-ray source ($KCu_\alpha$, $\lambda$=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 30°.

FIG. 1 shows a powder x-ray diffraction of Example 1 showing the material is amorphous.

EXAMPLE 2

Amorphous atorvastatin was prepared using the spray drying process of Example 1 except that the spray solution consisted of 1396 g of atorvastatin dissolved into 26524 g of methanol to form a 5 wt % solution. The spray solution was pumped to the spray drier at a rate of 170 g/min and at an atomization pressure of 10 atm (135 psig). The process resulted in the formation of amorphous atorvastatin. After drying, the material had a residual solvent level of less than 0.08%.

Figure 2:
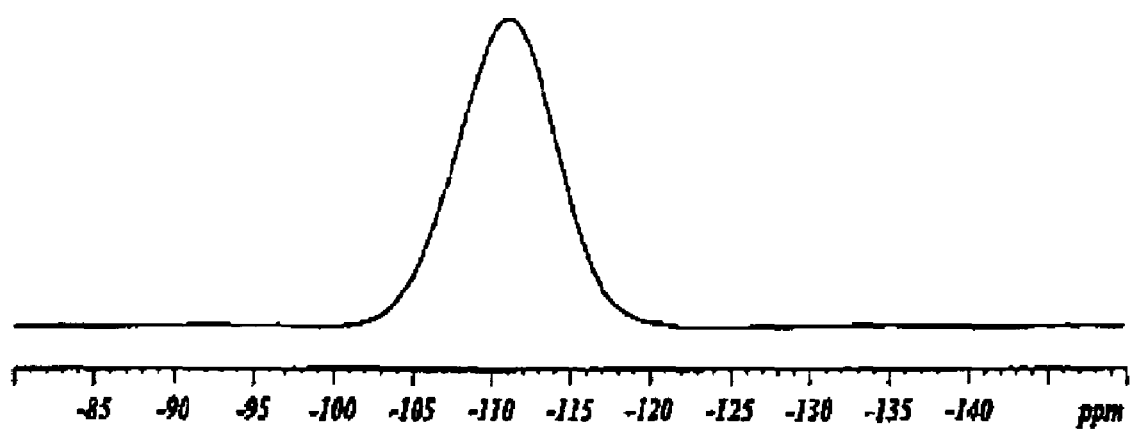
FIG. 2 shows a solid state $^{19}$F Nuclear Magnetic Resonance (NMR) spectra of the material of Example 2.

The material was evaluated using solid state $^{19}F$ NMR as follows: Approximately 75 mg of sample were tightly packed into a 4 mm ZrO spinner for each sample analyzed. One-dimensional $^{19}F$ spectra were collected at 295° K and ambient pressure on a Bruker-Biospin 4 mm BL CPMAS probe positioned into a wide-bore Bruker-Biospin Avance DSX 500 MHz NMR spectrometer. Rotors containing the analyzed samples were positioned at the magic angle and spun at 15.0 kHz, corresponding to their maximum specified spinning speed. The fast spinning speed minimized the intensities of the spinning side bands. Proton decoupling of approximately 70 kHz was applied during $^{19}F$ acquisition. To minimize the probe background signal a $^{19}F$ presaturation pulse was applied in the interleaved fashion. Additional background correction was achieved by subtracting the spectrum of a blank sample containing no fluorine atoms. The blank spectrum was acquired under identical conditions. For quantitative acquisition the recycle delay was set to 35 seconds. Typically, 300 scans were acquired to get adequate signal/noise (S/N). The spectra were referenced using an external sample of trifluoroacetic acid (diluted to 50% by volume with water), setting its resonance to −76.54 parts per million (ppm). The resulting broad peak shown in FIG. 2 confirms the material is amorphous.

Figure 3:
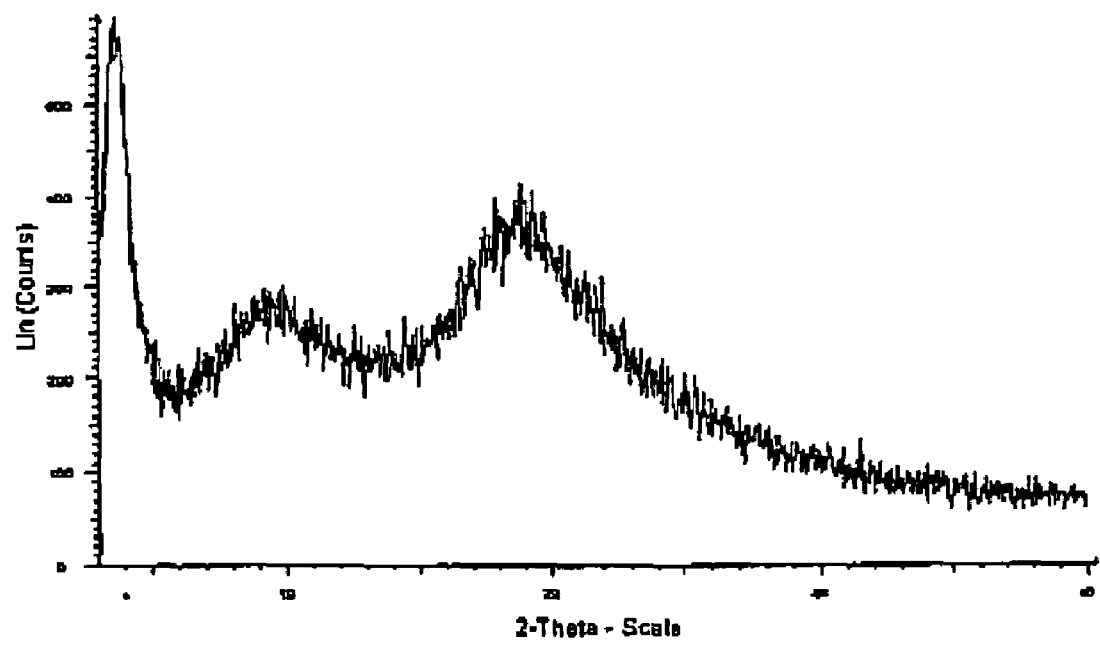
FIG. 3 shows a PXRD diffractogram of the material of Example 2.

The material was also evaluated using PXRD. The resulting diffractogram shown in FIG. 3 confirms the material is not crystalline, but is amorphous.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A process for forming amorphous atorvastatin, comprising:
    (a) dissolving atorvastatin in a solution comprising a hydroxylic solvent; and
    (b) rapidly evaporating said hyroxylic solvent from said solution to form amorphous atorvastatin, wherein at least 90 wt % of said solvent is evaporated by spray drying in less than five minutes.

2. The process of claim 1 wherein said hydroxylic solvent is selected from the group consisting of methanol, ethanol, n-propanol, and iso-propanol.

3. The process of claim 2 wherein said hydroxylic solvent is methanol.

4. The process of claim 1 wherein said evaporation in step (b) is carried out such that at least 90 wt % of said solvent is removed from said solution in less than one minute.

5. The process of claim 1 wherein said solvent is evaporated by spray-coating said solution onto a core, affording an atorvastatin coated core.

6. The process of claim 5 wherein said core is selected from the group consisting of non-pareil seeds, sugar beads, wax beads, glass beads, lactose, microcrystalline cellulose, polymer beads, starch, colloidal silica, calcium carbonate and calcium phosphate.

7. The process of claim 5 wherein said core is selected from the group consisting of a tablet, pill, multiparticulate and capsule.

8. The process of claim 7 wherein said tablet, pill, multipartculate or capsule contains atorvastatin.

9. The process of claim 1 wherein said amorphous atorvastatin is in the form of particles having a mean average diameter ranging in size from 1 μm to less than 500 μm.

10. The process of claim 1 wherein said amorphous atorvastatin is in the form of particles having a mean average diameter ranging in size from 1 μm to less than 100 μm.

11. The process of claim 5 wherein evaporation is carried out such that at least 90 weight % of said solvent is removed from said solution in less than five minutes.

12. The process of claim 5 wherein evaporation is carried out such that at least 90 weight % of said solvent is removed from said solution in less than one minutes.

13. The process of claim 1 wherein said amorphous atorvastatin has a residual solvent level of less than 1 wt %.

14. The process of claim 5 wherein said atorvastatin coated core has a residual solvent level of less than 1 wt %.

* * * * *

UNITED STATES PATENT AND TRADEMARK OFFICE
CERTIFICATE OF CORRECTION

PATENT NO.       : 7,655,692 B2                                            Page 1 of 1
APPLICATION NO.  : 10/828488
DATED            : February 2, 2010
INVENTOR(S)      : Lorenz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1464 days.

Signed and Sealed this

Twenty-third Day of November, 2010

David J. Kappos
*Director of the United States Patent and Trademark Office*